United States Patent [19]
De Faire

[11] Patent Number: 5,817,618
[45] Date of Patent: Oct. 6, 1998

[54] ANTI-MICROBIAL COMPOSITION

[75] Inventor: Johan De Faire, Vanholma, Sweden

[73] Assignee: Micro Active Protein AB, Göteborg, Sweden

[21] Appl. No.: 379,568

[22] PCT Filed: Aug. 17, 1993

[86] PCT No.: PCT/SE93/00684

§ 371 Date: Feb. 10, 1995

§ 102(e) Date: Feb. 10, 1995

[87] PCT Pub. No.: WO94/04033

PCT Pub. Date: Mar. 3, 1994

[30] Foreign Application Priority Data

Aug. 17, 1992 [SE] Sweden ................................. 9202362

[51] Int. Cl.⁶ .......................... A61K 38/00; A61K 38/14; C07K 17/00
[52] U.S. Cl. .................. 514/2; 514/8; 530/322; 530/395
[58] Field of Search ........................... 514/2, 8; 530/395, 530/322

[56] References Cited

U.S. PATENT DOCUMENTS 4,801,453  1/1989  Kosuge et al. ............................ 424/95

FOREIGN PATENT DOCUMENTS

WO 81/03124  11/1981  WIPO .
WO 88/04303  6/1988  WIPO .

OTHER PUBLICATIONS

Baldo et al., *Biochem. J.*, 175, 1978, 467–477.

Hawley's "The Condensed Chemical Dictionary" 10th Ed. (1981, Van Nostrand Reinhold Co.) p. 751.

*Primary Examiner*—Cecilia J. Tsang
*Assistant Examiner*—Bennett Celsa
*Attorney, Agent, or Firm*—Bacon & Thomas

[57] ABSTRACT

The present invention relates to an anti-microbial composition for non-pharmaceutical cleaning of contaminated materials, bodies and surfaces, especially contaminated liquids and gases. The composition comprises at least one anti-microbially active protein which has been isolated from mussels, preferably together with glycogen. A quick test for qualitative testing of possibly contaminated liquids, especially drinking water, is also disclosed. The quick test comprises a test tube containing a predetermined amount of the anti-microbial composition. A predetermined amount of the liquid is added to the test tube, shaken and allowed to sediment. The quality of the liquid is determined by a quality indicator extending along the tube.

46 Claims, 4 Drawing Sheets

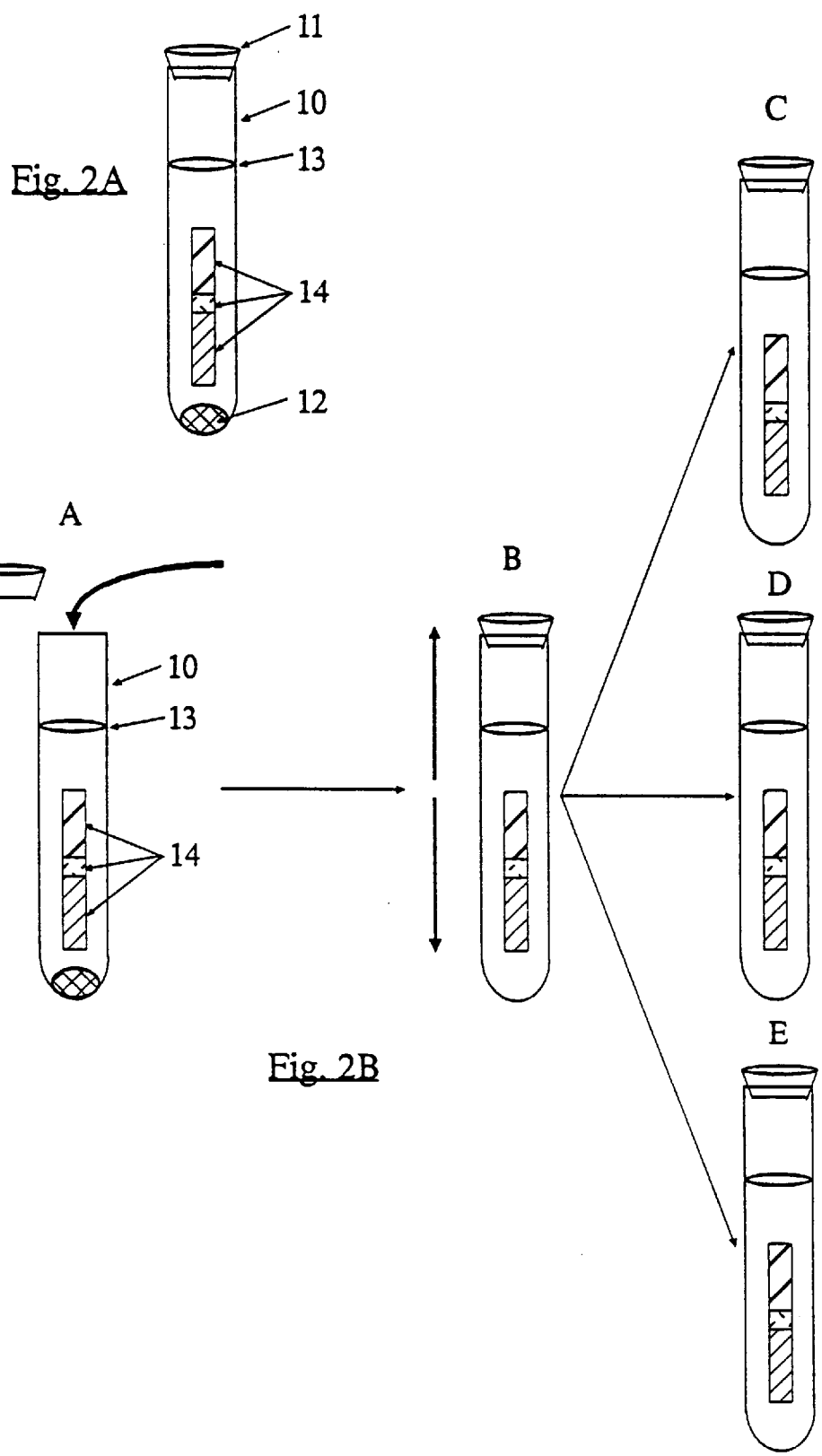

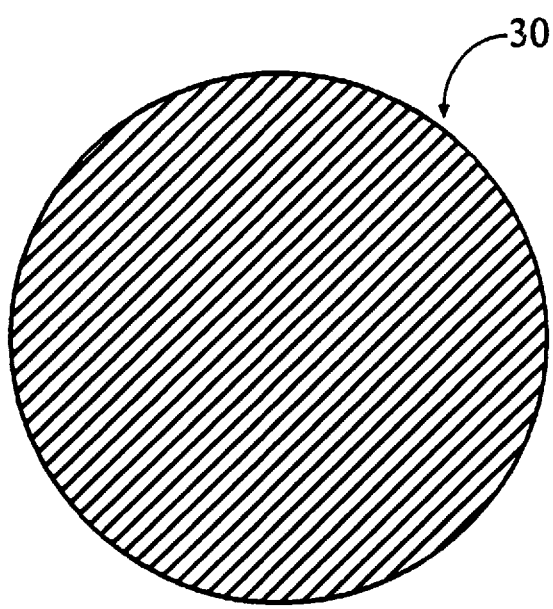
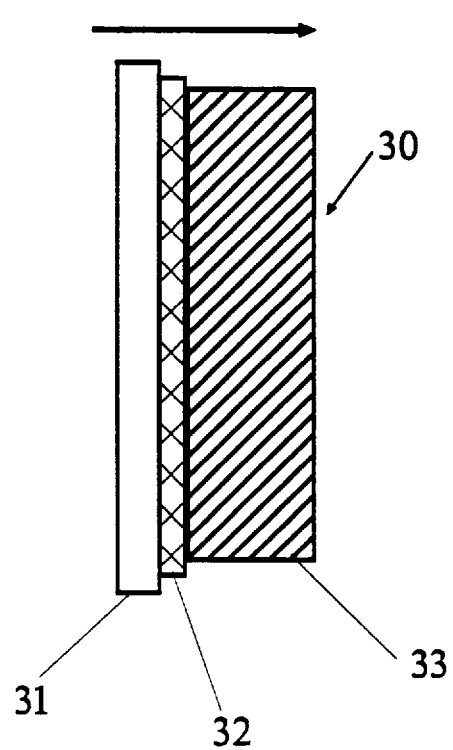
Fig. 3A
Fig. 3B

ANTI-MICROBIAL COMPOSITION

This application is a 371 of PCT/SE93/00684 filed Aug. 17, 1993.

TECHNICAL FILED

The present invention relates to anti-microbial treatment of microbially contaminated materials, bodies and surfaces in general, and in particular to anti-microbial treatment of microbially contaminated water and other liquids, gases and gas mixtures. The invention is also concerned with microbial testing of such materials, bodies and surfaces. As used herein the term "anti-microbial treatment" means that the treatment results in neutralization or inactivation of at least part of the contaminating microbes and preferably of all of the contaminating microbes. As used herein the term "microbes" includes toxins. For simplicity reasons the term "cleaning" is in this specification sometimes used instead of anti-microbial treatment.

BACKGROUND OF THE INVENTION

Microbial contamination is a great problem in many situations. One of the greatest global problems is the cleaning of water, both in developed and developing countries. Water, especially drinking-water, is a scarce resource which has to be re-used. Before using or re-using water as drinking-water it is highly desirable to make sure that the water is clean enough so that it does not constitute a health hazard for the humans or animals who have to drink it.

In the developed countries the problem with contaminated water, especially microbially contaminated water, is most pronounced in urban areas where the drinking-water often is circulated in very large distribution systems. It is usually required that the drinking-water should meet certain standards (prescribed by state, local or other jurisdiction) as regards e.g. physical, chemical and biological properties. Consequently, many procedures have been developed for mechanical, chemical and biological cleaning of water in order to meet these standards. Such cleaning is usually carried out at one or only a few central cleaning stations in the distribution network, and it quite often happens that the cleaned drinking-water becomes re-contaminated during the transport in the distribution system from the cleaning station to the end user. Another frequent problem is that one of the most efficient cleaning treatments, viz. the use UV-radiation, requires absolutely particle-free water in order to be effective. The presently available procedures for eliminating particles (such as sedimentation, flotation, sieving and the like) are, however, incapable of eliminating small microbial particles, so UV-radiation may not inactivate such particles even at the cleaning/disinfecting station.

In many developing countries, and also in parts of developed countries, there are many areas where no water cleaning facilities (central or local) are available, or are only very rudimentary. Since water is a basic need for humans and animals, water is drunk despite the fact that it is known that the water may be contaminated with poisonous or perhaps even lethal microbes. In such situations it would be highly desirable to have an easy-to-use means available for cleaning the water before drinking it, and in many situations already an easy-to-use test for determining whether or not the water is drinkable could be of great help.

There is also a continuing need for efficient anti-microbial agents in many other areas, e.g. for anti-microbial cleaning of surface-contaminated materials such as decontamination of process systems, instruments and equipment, filters for microbially contaminated air and other gases, etc.

A polypeptide fraction has been isolated from a bivalve, Tridacna maxima, by B. A. Baldo et al; Biochem. J. (1978), 175, p. 467–477 "Purification and Characterization of a Galactan-Reactive Agglutinin from The Clam Tridacna maxima (Röding and a Study of its Combining Site)". This isolated fraction is said to have interesting immunological properties. No other use is disclosed or suggested.

EP-A-50 636 discloses a specific polypeptide fraction which has been isolated from the body liquids of Mytilus mussels and the use thereof as an anti-microbial drug. The fraction in question in characterized as being capable of biospecifically binding at least one sialic acid in the presence of calcium ions. EP-A-50 636 does not disclose any non-pharmaceutical use of said fraction.

OBJECT OF THE INVENTION

It is a primary object of the invention to provide an improved anti-microbial agent for treatment of microbially contaminated materials, bodies and surfaces.

A specific object of the invention is the use of such cleaning agent for non-pharmaceutical cleaning of microbially contaminated water and other liquids.

A still more specific object of the invention is the use of said agent for the cleaning of microbially contaminated drinking-water.

A further object of the invention is to provide a non-pharmaceutical cleaning agent for anti-microbial cleaning of gases and gas mixtures.

A still further object of the invention is to provide a test kit and test method for quick testing of microbially contaminated materials, bodies and surfaces, especially contaminated water, in particular drinking-water.

These and other objects of the invention are achieved by means of the specific features which are indicated in the appended claims and which will be explained further in the following.

SUMMARY OF THE INVENTION

The invention is based on the unexpected discovery that certain proteins or protein fractions originating from mussels are capable of efficiently neutralizing, inhibiting and preventing propagation of virtually all microbial contaminants in liquids and gases, in particular in combination with glycogen. These proteins are thus active against bacteria, viruses, fungi, protozoa and also endotoxins by firmly binding such microbes in the presence of calcium ions or equivalent bivalent ions. The presence of glycogen enhances the neutralizing properties of the said protein or protein fraction.

A most interesting property of the neutralizing protein is that it is readily available in great amounts and can be prepared from inexpensive raw materials such as waste water from the mussels industry.

A further interesting property of the protein in question is that it is very resistant to both heat treatment and degradation by proteolytic trypsin and papain. It can, for example, be autoclaved at a temperature of about 120° for 20 minutes without loosing its anti-microbial, neutralizing properties.

These properties can thus be used as a means for purifying the protein from undesired by-products such as other proteins or protein fractions which are less resistant to heat and/or proteolytic enzymes.

SHORT DESCRIPTION OF THE DRAWINGS

FIG. 2A and 2B illustrate a quick test for qualitatively determining water quality according to the invention.

FIG. 3A and 3B are diagrammatic representations in front and side views respectively of one embodiment of a gas-mask filter for anti-microbial treatment of air according to the invention.

Example 1

Figure 1A:
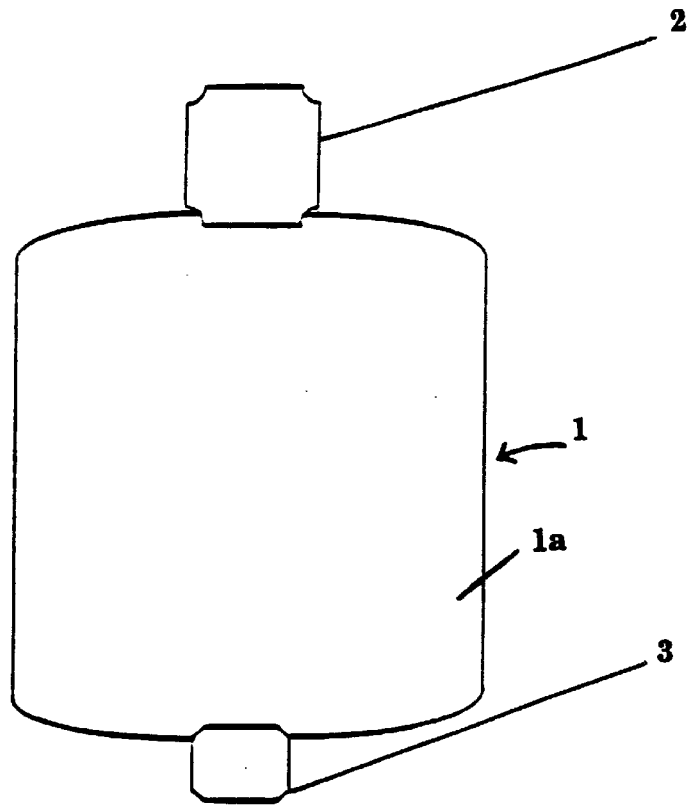
FIG. 1A and 1B are diagrammatic representations of one embodiment of a filter cartridge for treating contaminated liquids according to the invention.

Preparation of anti-microbial glycoprotein from Mytilus edulis

Boiling water from Mytilus edulis (waste water from the mussels industry) was allowed to flow through a cartridge of the type shown in FIG. 1 filled with hydroxylapatite as a matrix. The cartridge was then opened and emptied and the content was flushed with plenty of distilled water. The hydroxy-apatite was packed in columns and stepwise eluted with sodium chloride, 0.01–0.5 M. Fractions were tested for agglutination activity using a 3% solution of human erythrocytes in saline. Active fractions were pooled and concentrated 10 times by ultrafiltration and then dialyzed against 0.05 M tris-HCl, pH 8.5, 0.10 M NaCl, 0.005 M $CaCL_2$. A powder was obtained by lyophilization.

According to SDS-PAGE the product obtained had a molecular weight in the range of 12,000–30,000 with a peak at 14,400.

Example 2

Preparation of anti-microbial glycoprotein from Mytilus perna

The procedure described in Example 1 was repeated with the exception that Mytilus perna was used instead of Mytilus edulis. The lyophilized powder obtained showed the same molecular weight profile as the product of Example 1 determined by SDS-PAGE.

Example 3

Preparation of anti-microbial glycoprotein from pilgrim mussel

The procedure described in Example 1 was repeated with the exception that pilgrim mussle was used instead of Mytilus edulis. The lyophilized powder obtained showed the same molecular weight profile as the product of Example 1 determined by SDS-PAGE.

Example 4

Preparation of anti-microbial glycoprotein from hepato-pancreatic glands of Chlamys islandica The procedure described in Example 1 was repeated with the exception that frozen hepato-pancreatic glands of Chlamys islandica were used instead of Mytilus edulis in boiling water. The lyophilized powder obtained showed the same molecular weight profile as the product of Example 1 determined by SDS-PAGE.

Example 5

1 g of the powder prepared according to Example 1, 2, 3 or 4 was mixed with 100 ml of sewage water containing heterotrophic bacteria $1.4 \times 10^6$/100 ml; coliform bacteria $9.0 \times 10^6$/100 ml; E. coli $1.4 \times 10^6$/100 ml. A sediment was formed within 2 minutes, and after 2 hours the water was tested in conventional manner (cultivation). The water now only contained heterotrophic bacteria 860/100 ml; coliform bacteria<530/100 ml; E. coli 160/100 ml.

Example 6

Example 5 was repeated, but the powder was reconstituted in 0.1% of glycogen solution before mixing with the sewage water. The purpose of the addition of glycogen was to make more active sites available. The water only tested for the following bacterial contents/100 ml: heterotrophic bacteria<100; coliform bacteria<100; E. coli not detectable.

Example 7

100 mg of the powder obtained in Examples 1, 2, 3 or 4 was reconstituted in 0.1% glycogen solution and added to 100 ml of untreated well water containing micro-fungi in an amount of 118 cfu/100 ml. After 2 hours the water only tested for<1 cfu/100 ml.

Example 8

In the following Examples 8 and 9 the filter cartridge shown in FIG. 1A (outline) and FIG. 1B (longitudinal section) was used. The principal construction of the filter cartridge 1 is that it has a body 1a, an outlet 2 and an outlet 3. The liquid flow through the cartridge 1 can be caused by suction or pressure. For example, the inlet 2 may be connected to an inlet tube, faucet or pressure pump, and the outlet 3 may be a direct connection to a tube or to a suction pump or the like.

Figure 1B:
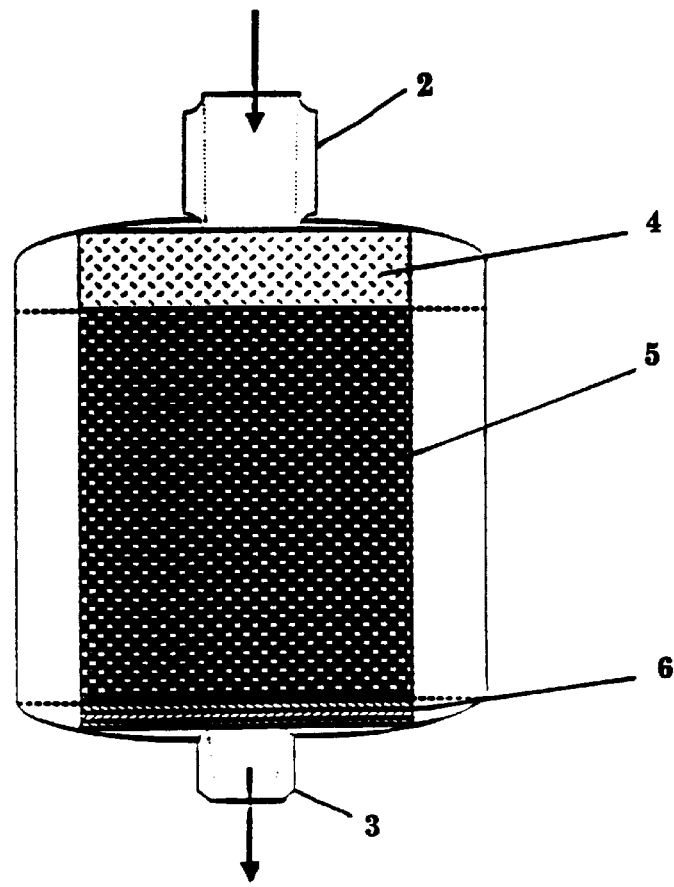

In the preferred embodiment shown in FIG. 1B the cartridge 1 has a suitable sieve 4 near the inlet 2. The sieve comprises a suitable sieving material such as metal web, fibers, fabrics, etc. or combinations thereof. Near the outlet 3 there is a net 6 for supporting a matrix 5 with bound protein.

100 mg of the powder obtained in Examples 1, 2, 3 or 4 was diluted and immobilized to activated carbon fiber (available from Osaka Gas, Japan). The fiber was packed in a cartridge of the type shown in FIG. 1 with a funnel and 500 ml of untreated well water to be tested was added. Untreated carbon fiber was used as reference. The filters worked on self-flow, 250 ml/min. The filtrate from both filters were collected and tested, with the following results.

Raw water (per 100 ml): heterotrophic bacteria $94 \times 10^3$; coliform bacteria 77; micro-fungi 8; actinomycetes 3.

Reference (per 100 ml): heterotrophic bacteria $68 \times 10^3$; coliform bacterial 33; micro-fungi 7; actinomycetes<1.

Treated fiber (per 100 ml): heterotrophic bacteria<100; coliform bacterial<1; micro-fungi<1; actinomycetes<1.

E. coli tested for<1 in all tests.

Example 9

Electrostatically bound glycoprotein to active carbon

The glycoprotein powder obtained in Example 1, 2, 3 or 4 was dissolved in water in a concentration of 1 mg/ml. 500 ml of this glycoprotein solution was mixed with 50 g active carbon granulate for 1h with stirring. The treated carbon powder was then washed with de-ionized water and air dried.

The obtained glycoprotein-coupled carbon was poured into a filter cartridge of the type shown in FIG. 1 using a funnel, and 50 liter of raw water was poured through the filter. Microbes and their toxins adhere to the active centers of the glycoprotein and remain firmly connected thereto for the useful life of the filter. The number of microorganisms (MO-status) was determined for the raw water, for the filter containing coupled glycoprotein and, as a control, for a filter containing the carbon filter without adhered glycoprotein. The test results were as follows:

| MO-status per 100 raw water | MO-status per 100 ml carbon filter | MO-status per 100 ml carbon filter with glycoprotein coupled thereto |
| --- | --- | --- |
| Heterotrophic bact.: $1.3 \times 10^6$ | Heterotrophic bact.: $8.6 \times 10^4$ | Heterotrophic bact.: 736 |
| Coliform bact.: 206 | Coliforma bact.: 191 | Coliform bact.: <1 |
| E. coli B: 48 | E. coli B: 43 | E. Coli B: <1 |

Example 10

Covalent binding of glycoprotein to solid matrixes

Glycoprotein according to the invention, e.g. the products prepared according to Examples 1, 2, 3 and 4, can be covalently bound to a plurality of solid matrixes by means of procedures which are known per se. Such matrixes can be natural materials (such as cotton, flux (linen), cellulose, etc.), synthetic materials (such as rayon, polyamide etc.), metals, salts, ions and macromolecules of inorganic or organic origin (such as sugars, apatite, etc.) or plastic polymer structures (ethylene, propylene, styrene, latex, etc.). The matrix is preferably activated by attachment of an active chemical group such as an amino group to the surface thereof. The glycoprotein can be bound to the active group either directly or, alternatively, by means of a so-called spacer having one of its ends covalently bound to the active group on the matrix surface, with its other ends covalently binding specifically to the glycoprotein with maintained activity thereof. The matrix may be a surface, granula, spheres, fiber or woven structures or the like, which may be packed and used as in Example 9.

Polyethylene/polypropylene fiber, 30 g/m, was activated/coupled using the above disclosed procedure. 18 g coupled fiber, 240 mg glycoprotein was used per filter cartridge. Microbial testing was performed as in Example 9. The results were as follows:

| MO-status per 100 raw water | MO-status per 100 ml untreated matrix filter | MO-status per 100 ml matrix filter with glycoprotein coupled thereto |
| --- | --- | --- |
| Heterotrophic bact.: $1.3 \times 10^6$ | Heterotrophic bact.: $1.2 \times 10^6$ | Heterotrophic bact.: 622 |
| Coliform bact.: 206 | Coliform bact.: 203 | Coliform bact.: <1 |
| E. coli B: 48 | E. coli B: 47 | E. coli B: <1 |

Example 11

Free glycoprotein for precipitation of microbes in solutions 100 mg of the glycoprotein prepared as in Example 1, 2, 3 or 4 was dissolved in 100 ml sterile water and then mixed with 10 liter raw water. A water sample was taken after two hours and the precipitate was collected and washed with sterile water. The MO-status was determined for the raw water, the water sample and for the precipitate. The following results were obtained.

| MO-status per 100 ml raw water | MO-status per 100 ml water sample | MO-status precipitate |
| --- | --- | --- |
| Heterotrophic bact.: $1.3 \times 10^6$ | Heterotrophic bact.: $<1.2 \times 10^3$ | Heterotrophic bact.: Total $<1 \times 10^3$ |
| Coliform bact.: 206 | Coliform bact.: <1 | |
| E coli B: 48 | E coli B: <1 | |

Example 12

Quick test for microbial contamination

The glycoprotein prepared according to Example 1, 2, 3 or 4, which has been bound to a carrier of colloidal latex-beads by means of the procedure described in Example 10, can be used as a quick test/qualitative test of water, aqeuous solutions, other liquids and body liquids as regards microbial contamination.

FIG. 2 shows an example of an embodiment of a quick test tube according to the invention, which comprises the very tube 10 provided with a sealing plug 11. The tube comprises a pre-selected amount a protein-carrier 12 according to the invention, and it has a quality indicator 14 as well as a marking 13 indicating the level to which the tube should be filled with liquid to be tested, corresponding to a suitable volume, e.g. 5 cm$^3$.

FIG. 2A illustrates a suitable procedure for carrying out the quick test. Four reference solutions containing (A) sterile water, (C) $2.8 \times 10^3$, (D) $7.4 \times 10^3$ and (E) $1.7 \times 10^4$ microorganisms/100 ml were tested respectively. 5 ml of each reference solution was added to a great excess of glycoprotein-latex (glycoprotein-carrier) in the test tube 10 which had a volume marking 13 (in the present case 5 cc) and a quality indicator 14. The test tube was shaken gently (as illustrated by the arrows in FIG. 2A) and was then allowed to rest for e.g. 30 seconds or 2 minutes to complete the precipitation. The level of the precipitate in the test tube is a function of the microbial concentration in the tested liquid. The height of the precipitate was as follows: Tube A(B): no precipitation, tube C: 8 mm, tube D: 15 mm, and tube E: 22 mm.

The quality indicator may e.g. be designed to show that these readings correspond to "clean", "contaminated but drinkable", "barely drinkable" and "undrinkable" water.

As mentioned above the anti-microbial composition according to the invention can also be used for treating contaminated air or other gases. FIG. 3A and 3B show the principal construction of a breathing filter 30 for fitting into a gasmask housing. The filter 30 comprises a front 31 with breathing holes, an O-ring seal 32 and a network structure 33 carrying the anti-microbial composition according to the invention (matrix with protein).

Figure 4:
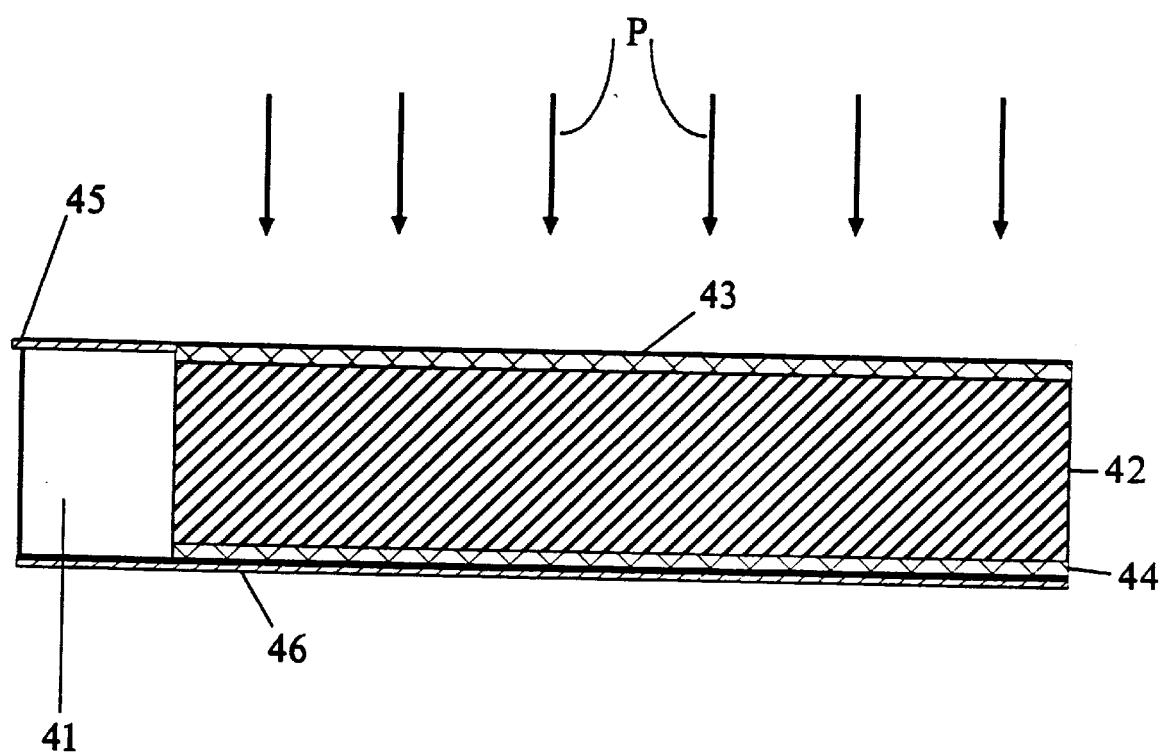
FIG. 4 is a diagrammatic representation in cross-section of one embodiment of a filter unit for purification of air and other gases according to the invention.

FIG. 4 shows the principal construction of a filter unit or module 40, for purification of air and other gases. The module 40 comprises a unit frame 41 carrying a matrix with protein 42 carried by top and bottom support grids 43 and 44 respectively. 45 and 46 represent suitable gaskets. The arrows P illustrate the flow of contaminated gas to be purified in the filter unit 41.

I claim:

1. An anti-microbial composition which comprises at least one anti-microbially active protein which has been isolated from mussels and a glycogen additive which is added to said isolated protein to produce an admixture containing said isolated protein and said additive, said additive being added in an amount so that said composition contains at least one molecule of added glycogen per molecule of ant-microbially active protein isolated from said mussels.

2. An anti-microbial composition according to claim 1 wherein said at least one anti-microbially active protein has been isolated from mussels selected from the group consisting of mussels of the Mytilus species, mussels of the Perna species, Chlamys islandica and Cyprina islandica.

3. An anti-microbial composition according to claim 1, wherein said at least one anti-microbially active protein has been isolated from mussels selected from the group consisting of Mytilus edulis, Mytilus perna, Perna perna and pilgrim mussel.

4. An anti-microbial composition according to claim 1, wherein said composition comprises bi-valent metal ions.

5. The composition of claim 4 wherein said bi-valent metal ions are calcium ions.

6. An anti-microbial composition according to claim 1, wherein said at least one anti-microbially active protein is resistant to heating to at least 100° C. without losing its anti-microbial activity.

7. The composition of claim 6 wherein said anti-microbially active protein is resistant to autoclaving at about 120° C. for 20 minutes without losing its anti-microbial activity.

8. An anti-microbial composition according to claim 1, wherein said anti-microbial composition is stable (not degraded) in the presence of at least one proteolytic enzyme selected from the group consisting of bovine trypsin, porcine trypsin and papain.

9. An anti-microbial composition according to claim 1, wherein said composition has the form of a powder, solution or suspension.

10. An anti-microbial composition according to claim 1, wherein said composition is covalently bound, or otherwise connected to a carrier.

11. An anti-microbial composition according to claim 1, wherein said at least one anti-microbially active protein has a molecular weight in the range of 12,000–30,000 wherein said molecular weight is determined by SDS-PAGE .

12. The composition of claim 11 wherein said anti-microbially active protein is a protein having a molecular weight which is about 14,400 or about 30,000.

13. An anti-microbial composition according to claim 1, wherein said composition acts by neutralizing or inhibiting the microbial effect of the microbes, including toxins, and/or by preventing propagation of the microbes.

14. An anti-microbial composition according to claim 1, wherein said neutralization, inhibition or prevention of propagation is achieved by the capability of said protein to firmly bind said microbes to its active sites.

15. An anti-microbial composition according to claim 1, wherein said composition is active against at least one microbe selected from the group consisting of bacteria, viruses, fungi, protozoa and endotoxins.

16. The composition of claim 15 wherein said composition is active against bacteria, viruses, fungi, protozoa and endotoxins.

17. An anti-microbial composition according to claim 1, wherein at least one of said anti-microbially active protein is a glycoprotein.

18. An anti-microbial composition according to claim 1, wherein said composition is capable of binding to hydroxy apatite.

19. An anti-microbial composition according to claim 1 wherein said anti-microbially active protein is a glycoprotein.

20. The method for treating a microbially contaminated fluid selected from the group consisting of water and other liquids and contaminated gases, which comprises contacting said contaminated fluid with the composition of claim 1.

21. The method of claim 20 wherein said fluid is drinking water.

22. The method of claim 21 wherein said composition is mixed with said water thereby causing precipitation of said microbes.

23. A method of flotating microbial contaminants from drinking water to remove said contaminants from said drinking water, which comprises adding a flotation agent to said water, flotating said contaminants contained in said water and then removing said floating contaminants from said water, wherein said flotation agent is a composition according to claim 1.

24. An anti-microbial composition which consists essentially of at least one anti-microbially active protein which has been isolated from mussels and a glycogen additive which is added to said isolated protein to produce an admixture containing said isolating protein and said additive; said additive being added in an amount so that said composition contains at least one molecule of added glycogen per molecule of anti-microbial active protein isolated from said mussels.

25. An anti-microbial composition according to claim 24 wherein said at least one anti-microbially active protein has been isolated from mussels selected from the group consisting of mussels of the Mytilus species, mussels of the Perna species, Chlamys islandica and Cyprina islandica.

26. An anti-microbial composition according to claim 24 wherein said at least one anti-microbially active protein has been isolated from mussels selected from the group consisting of Mytilus edulis, Mytilus perna, Perna perna and pilgrim mussel.

27. An anti-microbial composition according to claim 24 wherein said composition further includes bi-valent metal ions.

28. The anti-microbial composition according to claim 29 wherein said bi-valent metal ions a re calcium ions.

29. An anti-microbial composition according to claim 24 wherein said at least one anti-microbially active agent is resistant to heating to at least 100° C. without losing its anti-microbial activity.

30. The anti-microbial composition according to claim 29 wherein said anti-microbially active agent is resistant to autoclaving at about 120° C. for 20 minutes without losing its anti-microbial activity.

31. An anti-microbial composition according to claim 24 wherein said anti-microbial composition is stable (not degraded) in the presence of at least one proteolytic enzyme selected from the group consisting of bovine trypsin, porcine trypsin and papain.

32. An anti-microbial composition according to claim 24 wherein said composition is in the form of a powder, solution or suspension.

33. An anti-microbial composition according to claim 24 wherein said composition is covalently bound, or otherwise connected to a carrier.

34. An anti-microbial composition according to claim 24 wherein said at least one anti-microbially active protein has a molecular weight in the range of 12,000–30,000 wherein said molecular weight is determined by SDS-PAGE.

35. The anti-microbial composition according to claim 34 wherein said at least one anti-microbially active protein has a molecular weight about 14,400 or about 30,000.

36. An anti-microbial composition according to claim 24 wherein said composition acts by neutralizing or inhibiting the microbial effect of the microbes, including toxins, and/or by preventing propagation of the microbes.

37. An anti-microbial composition according to claim 36 wherein said neutralization, inhibition or prevention of propagation is achieved by the capability of said protein to firmly bind said microbes to its active sites.

38. An anti-microbial composition according to claim 24 wherein said composition is active against at least one microbe selected from the group consisting of bacteria, viruses, fungi, protozoa and endotoxins.

39. The anti-microbial composition according to claim 38 wherein said composition is active against bacteria, viruses, fungi, protozoa and endotoxins.

40. An anti-microbial composition according to claim 24 wherein at least one of said anti-microbially active protein is a glycoprotein.

41. An anti-microbial composition according to claim 24 wherein said composition is capable of binding to hydroxy apatite.

42. An anti-microbial composition according to claim 24 wherein said anti-microbially active protein is a glycoprotein.

43. A method for treating microbially contaminated fluid selected from the group consisting of water and other liquids and contaminated gases, which comprises contacting said water, liquid or gas with the composition of claim 24.

44. The method of claim 43 wherein said fluid is drinking water.

45. The method of claim 44 wherein said composition is mixed with said water thereby causing precipitation of said microbes.

46. A method of flotating microbial contaminants from drinking water to remove said contaminants therefrom, which comprises adding a flotation agent to said water, floating said contaminants and then removing said flotated contaminants from said water; wherein said flotation agent is a composition according to claim 24.

* * * * *